(12) United States Patent
Ziolo et al.

(10) Patent No.: US 10,335,202 B2
(45) Date of Patent: Jul. 2, 2019

(54) LOCKABLE PEDICLE FASTENER

(71) Applicant: BLACKSTONE MEDICAL, INC., Lewisville, TX (US)

(72) Inventors: Tara Ziolo, Hewitt, NJ (US); Michael A. Hammer, Cranford, NJ (US); John Lovell, North Bergen, NJ (US); Francesco A. Larosa, Neptune, NJ (US); Nelson Li, Celina, TX (US)

(73) Assignee: BLACKSTONE MEDICAL, INC., Lewisville, TX (US)

( * ) Notice: Subject to any disclaimer, the term of this patent is extended or adjusted under 35 U.S.C. 154(b) by 354 days.

(21) Appl. No.: 14/593,384

(22) Filed: Jan. 9, 2015

(65) Prior Publication Data

US 2015/0134004 A1 May 14, 2015

Related U.S. Application Data

(62) Division of application No. 14/075,795, filed on Nov. 8, 2013.

(51) Int. Cl.
*A61B 17/70* (2006.01)

(52) U.S. Cl.
CPC ...... *A61B 17/7037* (2013.01); *A61B 17/7032* (2013.01); *A61B 17/7035* (2013.01)

(58) Field of Classification Search
CPC .... A61B 17/8605–866; A61B 17/7001; A61B 17/7032–7046
See application file for complete search history.

(56) References Cited

U.S. PATENT DOCUMENTS

| | | | | |
|---|---|---|---|---|
| 5,443,467 A | * | 8/1995 | Biedermann | A61B 17/7032 606/65 |
| 5,928,231 A | * | 7/1999 | Klein | A61B 17/7049 606/60 |
| RE42,545 E | | 7/2011 | Ralph et al. | |
| 9,247,965 B2 | * | 2/2016 | Biedermann | A61B 17/70 |
| 2004/0097933 A1 | * | 5/2004 | Lourdel | A61B 17/7037 606/266 |
| 2010/0094349 A1 | | 4/2010 | Hammer et al. | |

(Continued)

FOREIGN PATENT DOCUMENTS

EP  1316294 A2  6/2003

OTHER PUBLICATIONS

International Search Report and Written Opinion, PCT/US2014/064316, dated Apr. 14, 2015, 11 pages.

(Continued)

*Primary Examiner* — Ellen C Hammond
*Assistant Examiner* — Tessa M Matthews
(74) *Attorney, Agent, or Firm* — Haynes and Boone, LLP

(57) ABSTRACT

A spinal fixation system comprising at least one fastener having a fastener head at a proximal end and at least one body. The body comprises a rod receiving channel for receiving a fixation rod, a pressure cap for engaging the fastener head, and a fastener head receiving chamber for retaining the fastener head within the body. The fastener head receiving chamber allows for multi-axial movement of the body in relation to the fastener when the pressure cap is disengaged from the fastener head. The body is secured in a mono-axial position in relation to the fastener when the pressure cap is biased against the fastener head.

15 Claims, 7 Drawing Sheets

(56) References Cited

U.S. PATENT DOCUMENTS

| | | |
|---|---|---|
| 2010/0152785 A1 | 6/2010 | Forton et al. |
| 2010/0298891 A1 | 11/2010 | Jackson |
| 2011/0009911 A1 | 1/2011 | Hammill, Sr. et al. |
| 2011/0106178 A1 | 5/2011 | Schwab |
| 2011/0152949 A1* | 6/2011 | Biedermann ...... A61B 17/7037 606/305 |
| 2011/0160778 A1 | 6/2011 | Elsbury |
| 2011/0257690 A1* | 10/2011 | Rezach ............. A61B 17/7037 606/302 |
| 2012/0095516 A1* | 4/2012 | Dikeman ........... A61B 17/7032 606/305 |
| 2012/0143260 A1 | 6/2012 | Gunn et al. |
| 2012/0209335 A1* | 8/2012 | Termyna ........... A61B 17/7037 606/300 |
| 2012/0209336 A1* | 8/2012 | Jackson ............. A61B 17/7037 606/305 |
| 2012/0232598 A1* | 9/2012 | Hestad ............... A61B 17/7037 606/305 |
| 2012/0283789 A1* | 11/2012 | Biedermann ...... A61B 17/7034 606/308 |
| 2013/0060292 A1 | 3/2013 | Jackson |
| 2013/0096622 A1* | 4/2013 | Biedermann .......... A61B 17/70 606/279 |
| 2014/0012337 A1* | 1/2014 | Biedermann ........ A61B 17/844 606/328 |
| 2014/0142634 A1* | 5/2014 | Schlaepfer ........... A61B 17/704 606/278 |
| 2014/0236238 A1* | 8/2014 | Ark .................... A61B 17/7037 606/278 |
| 2015/0080960 A1* | 3/2015 | Biedermann ...... A61B 17/7037 606/278 |
| 2015/0119940 A1* | 4/2015 | Jackson ............. A61B 17/7076 606/266 |

OTHER PUBLICATIONS

Extended European Search Report dated Sep. 26, 2017 in connection with European Application No. 14860447.3, 10 pages.
Examination Report dated Jul. 26, 2018 in connection with Australian Application No. 2014346778, 6 pages.

\* cited by examiner

LOCKABLE PEDICLE FASTENER

CROSS-REFERENCE TO RELATED APPLICATIONS

This is a divisional application of U.S. application Ser. No. 14/075,795, which was filed on Nov. 8, 2013 and is incorporated herein by reference in its entirety.

TECHNICAL FIELD

The embodiments described and claimed herein relate to a spinal fixation system comprising a multi-axial pedicle screw that is operable to be locked in a mono-axial position.

BACKGROUND ART

Various spinal fixation systems involving connecting fastener elements (e.g., pedicle screws) to elongated supports (e.g., fixation rods) for the purposes of vertebral fixation have been proposed. Two varieties include mono-axial fastener elements and multi-axial fastener elements. Both have distinct benefits. Accordingly, there is a need for spinal fixation systems involving connecting fastener elements (e.g., pedicle screws) to elongated supports (e.g., fixation rods) that offer the benefits of both mono-axial elements and multi-axial elements.

BRIEF SUMMARY

The embodiments described and claimed herein relate to a spinal fixation system that includes a body and a fastener, wherein a pressure cap is operable to provide the benefits of both a multi-axial assembly and a mono-axial assembly. In one embodiment, the spinal fixation system comprises at least one screw having a screw head at a proximal end and wherein the screw head comprises a substantially spherical surface. It also comprises at least one body, wherein the body has a proximal portion and a distal portion. The proximal portion comprises a rod receiving channel for receiving a fixation rod, an external attachment feature, and a pressure cap disposed at a distal end of the proximal portion wherein a distal end of the pressure cap comprises an interior surface contoured to fit against the substantially spherical surface of the screw head. The distal portion comprises an internal attachment feature for engaging the external attachment feature of the proximal portion, wherein the engaging of the internal attachment feature with the external attachment feature secures the upper body to the lower body, a screw head receiving chamber disposed at a distal end of the distal portion for retaining the screw head within the body, and an external surface operable to engage a drive tool that operates to join the internal attachment feature with the external attachment feature and further cause the pressure cap to apply a bias against the screw head. The screw head receiving chamber allows for multi-axial movement of the body in relation to the screw when the pressure cap is disengaged from the screw head. And the body can be secured in a mono-axial position in relation to the screw when the pressure cap is biased against the screw head.

In another embodiment, the spinal fixation system comprises at least one screw having a screw head at a proximal end and wherein the screw head comprises a substantially spherical surface, and at least one body comprising a rod receiving channel for receiving a fixation rod, an internal attachment feature, and a screw head receiving chamber disposed at a distal end of the body for retaining the screw head within the body. The spinal fixation system further comprises at least one pressure cap disposed at a proximal end of the screw head receiving chamber. The pressure cap comprises a distal end with an interior surface contoured to fit against the substantially spherical surface of the screw head for engaging the screw head, an external attachment feature for engaging the internal attachment feature of the body, wherein the engaging of the internal attachment feature with the external attachment feature secures the body to the pressure cap and allows the pressure cap to travel distally until the distal end is biased against the screw head, and an internal surface operable to engage a driving tool operable to adjust the position of the pressure cap in a proximal or distal direction. The screw head receiving chamber allows for multi-axial movement of the body in relation to the screw when the pressure cap is disengaged from the screw head. And the body is secured in a mono-axial position in relation to the screw when the pressure cap is biased against the screw head.

In another embodiment, the spinal fixation system comprises at least one screw having a screw head at a proximal end and wherein the screw head comprises a substantially spherical surface and at least one body. The body has a proximal end and a distal end and further comprises a rod receiving channel for receiving a fixation rod wherein the rod receiving channel is disposed adjacent the proximal end of the body, and a screw head receiving chamber disposed adjacent the distal end of the body. The rod receiving channel and the screw head receiving chamber are operatively connected. The spinal fixation system further comprises a pressure cap for engaging the screw head. The pressure cap comprises a proximal portion disposed at least partially within the rod receiving channel, a distal portion disposed at least partially within the screw head receiving chamber, at least two lateral sides extending from the proximal portion to the distal portion, a screw head interface disposed adjacent to the distal portion of the pressure cap, a rod receiving surface disposed proximal to the screw head interface, and an aperture extending from the rod receiving surface to the screw head interface. The pressure cap is operable to travel from within the rod receiving channel towards the screw head receiving chamber of the body when the fixation rod or a tool is used to apply a distal bias to the rod receiving surface such that the screw head interface of the pressure cap is biased against the screw head in the screw head receiving chamber. The spinal fixation system also comprises a locking mechanism for securing the pressure cap in a biased position against the screw head. The screw head receiving chamber allows for multi-axial movement of the body in relation to the screw when the pressure cap is disengaged from the screw head. And the body is secured in a mono-axial position in relation to the screw when the pressure cap is biased against the screw head.

In another embodiment, the spinal fixation system comprises at least one fastener having a fastener head at a proximal end, and at least one body. The body comprises a rod receiving channel for receiving a fixation rod, a pressure cap for engaging the fastener head, and a fastener head receiving chamber for retaining the fastener head within the body. The fastener head receiving chamber allows for multi-axial movement of the body in relation to the fastener when the pressure cap is disengaged from the fastener head. The body is secured in a mono-axial position in relation to the fastener when the pressure cap is biased against the fastener head.

BRIEF DESCRIPTION OF THE SEVERAL VIEWS OF THE DRAWINGS

These and other features, aspects, objects, and advantages of the embodiments described and claimed herein will become better understood upon consideration of the following detailed description, appended claims, and accompanying drawings where:

Figure 1:
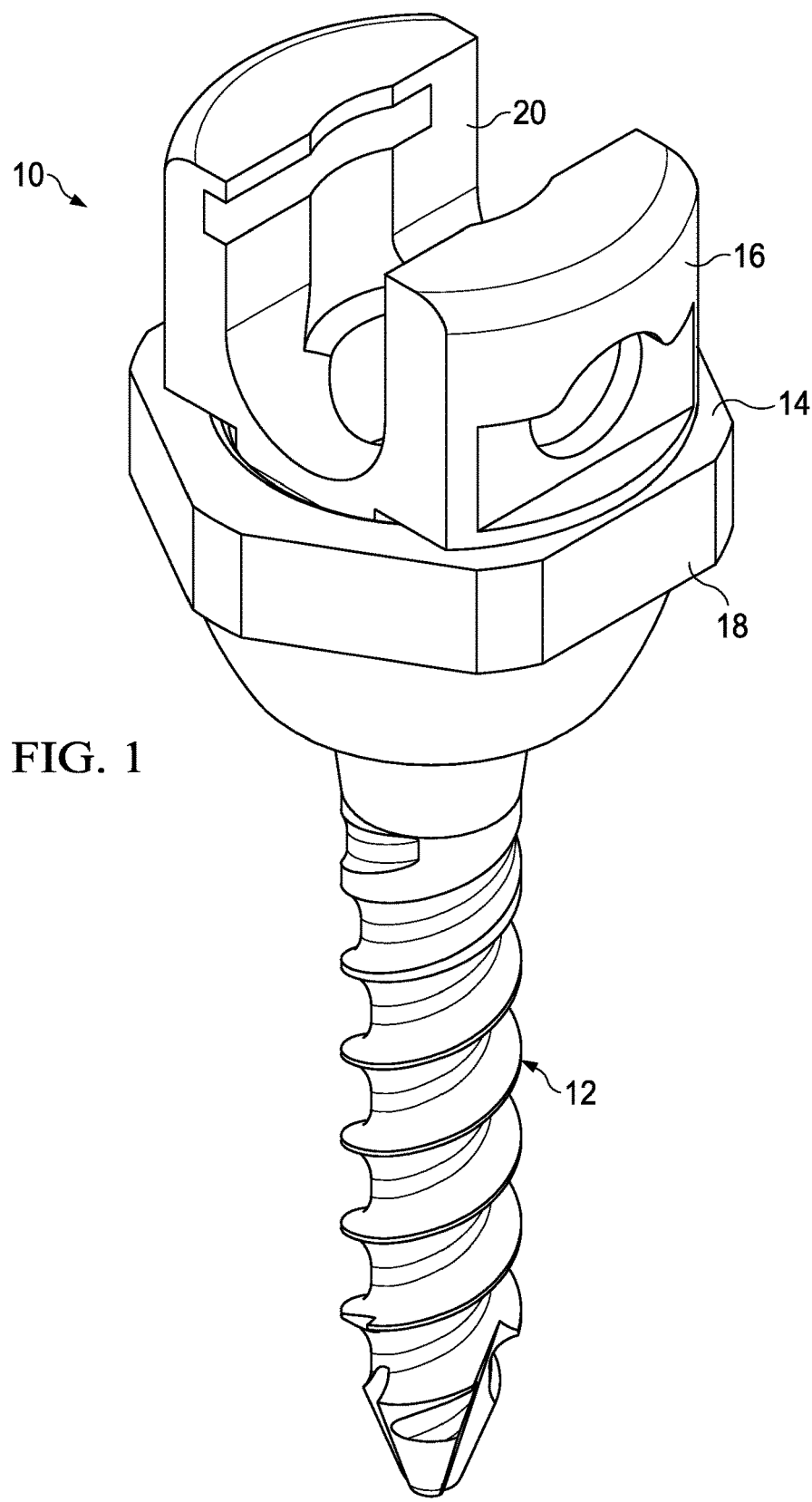
FIG. 1 is a perspective view illustrating one embodiment of a lockable fastener assembly.

It should be understood that the drawings are not necessarily to scale and that the embodiments are sometimes illustrated by graphic symbols, phantom lines, diagrammatic representations and fragmentary views. In certain instances, details which are not necessary for an understanding of the embodiments described and claimed herein or which render other details difficult to perceive may have been omitted. It should be understood, of course, that the inventions described herein are not necessarily limited to the particular embodiments illustrated. Indeed, it is expected that persons of ordinary skill in the art may devise a number of alternative configurations that are similar and equivalent to the embodiments shown and described herein without departing from the spirit and scope of the claims.

Like reference numerals will be used to refer to like or similar parts from Figure to Figure in the following detailed description of the drawings.

DETAILED DESCRIPTION

Referring first to FIG. 1, a perspective view illustrating one embodiment of a lockable fastener assembly 10 is shown. In one embodiment the assembly 10 comprises a fastener 12 and a body 14. The fastener 12 may be a screw in some embodiments. In one embodiment, the fastener 12 may be a bone screw. And in another embodiment the fastener 12 may be a bone screw for attachment to a pedicle of a vertebral body. In other embodiments the fastener 12 may be any other type of fastener for attachment to a bone. In one embodiment, such as shown in FIG. 1, the body 14 is further comprised of a proximal portion 16 and a distal portion 18. As shown in FIG. 1, the proximal portion 16 includes a rod receiving channel 20 for receiving a fixation rod.

Figure 2:
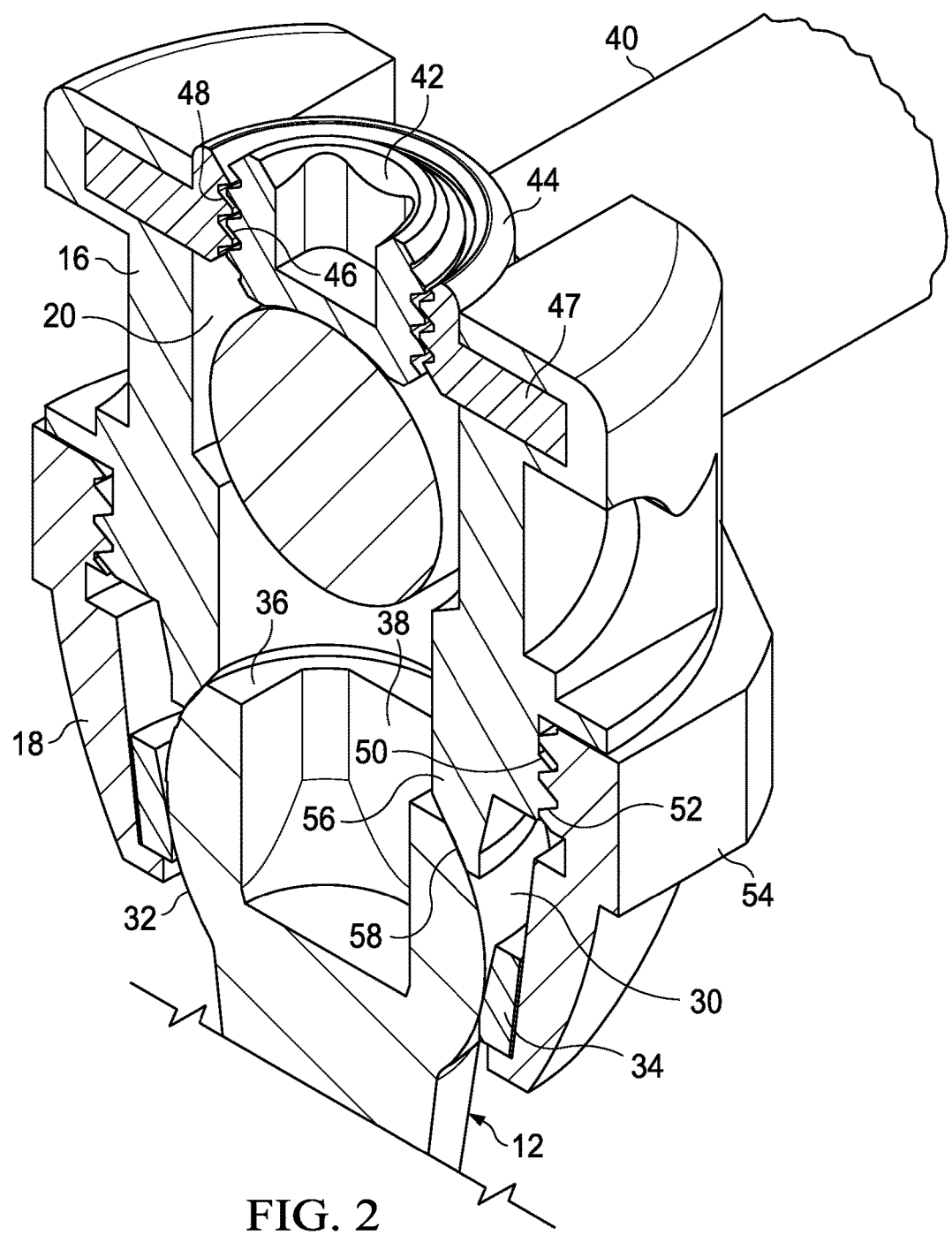
FIG. 2 is a longitudinal cross-sectional view of a lockable fastener assembly and fixation rod.

FIG. 2 is a longitudinal cross-sectional view of the lockable fastener assembly from FIG. 1. As can be seen in the embodiment shown in FIG. 2, the distal portion 18 includes a fastener head receiving chamber 30 for receiving the head 32 of a fastener 12. The fastener head receiving chamber 30 may have a tapered shape that narrows at the distal end of the fastener head receiving chamber 30 to fit against the fastener head 32. A layer of retaining material 34 may line the interior surface of the fastener head receiving chamber 30, wherein the retaining material is operable to facilitate retention of the fastener head 32 within the fastener head receiving chamber 30. The retaining material 34 may be composed of a softer grade of material than the material composition of the body 14 and may provide a friction fit between the fastener head receiving chamber 30 and the fastener head 32. In certain embodiments, the fastener head receiving chamber 30 may further comprise a constriction element, such as a spring-clip, that operates to create a friction fit between an interior surface of the fastener head receiving chamber 30 and the fastener head 32. In one embodiment, the fastener head 32 may have a substantially spherical shape, wherein the substantially spherical shape may include a flattened proximal face 36, as shown in FIG. 2. In one embodiment, the fastener head 32 may include a drive tool receiving recess 38 for receiving a drive tool which operates to drive the fastener into the bone. The rod receiving channel 20 and the fastener head receiving chamber 30 may be operatively connected to allow a drive tool to pass through to the fastener head 32 and apply torque thereto.

Also shown in FIG. 2 is the fixation rod 40 positioned in the rod receiving channel 20. The fixation rod 40 rests at the distal end of the rod receiving channel 20. The fixation rod 40 can be secured in place in the rod receiving channel 20 using a compression element such as the set screw 42 shown in FIG. 2. The set screw 42 may be attached to a blocker 44 that is inserted into a blocker receiving portion 47 of the proximal portion 16. The set screw 42 may include external threads 46 for engaging internal threads 48 of the blocker. In this embodiment the set screw 42 can be engaged by a drive tool for tightening against the fixation rod 40. In this way the set screw 42 is operable to retain the fixation rod 40 in the rod receiving channel 20 and secure the fixation rod 40 in a fixed position. In other embodiments, the set screw 42 may be attached to the blocker 44 by attachment means other than internal and external threads. And in further embodiments, the compression element for retaining the rod in a fixed position may be comprised of a mechanism other than a set screw and blocker combination. For example, in some embodiments, the proximal portion 16 may include internal threads disposed adjacent to the proximal end of the rod receiving channel 20. A set screw may then attach directly to the proximal portion 16 by attachment via its own external threads to the proximal portion's internal threads, without the need for a blocker. In even further embodiments, the compression element may be configured as a cap that attaches to the proximal portion 16.

As shown in FIG. 2, the proximal portion 16 may have an external attachment feature 50 that engages an internal attachment feature 52 of the distal portion 18. The engagement of the external attachment feature 50 with the internal attachment feature 52 secures the proximal portion 16 to the distal portion 18. In one embodiment, the external attachment feature 50 is an external thread and the internal attachment feature 52 is an internal thread. Such threads could be of any variety of attachment threads, such as buttress threads or any other thread common in the medical industry. The distal portion 18 may also have an external surface 54 adapted for engaging a drive tool. The external surface 54 may comprise multiple flat sides to form a shape such as octagonal, hexagonal, pentagonal, square, or triangle. The external surface 54 can be of any other shape or composition such that it is operable to be engaged by a drive tool.

The embodiment shown in FIG. 2 also includes a pressure cap 56 located at the distal end of the proximal portion 16. The pressure cap 56 has an interior surface 58 that is contoured to fit against the fastener head 32. For example, when the fastener head 32 has a substantially spherical shape as shown in FIG. 2, the interior surface 58 of the pressure cap 56 will be contoured to fit against the substantially spherical surface of the fastener head 32. When the pressure cap 56 is disengaged from the fastener head 32, the fit between the interior surface 58 of the pressure cap 56 and the fastener head 32 allows the body 14 to pivot along multiple axes in relation to the fastener 12. This multi-axial movement allows the fastener to be placed in the vertebral body much easier than a mono-axial fixation system. A mono-axial fixation system requires very accurate placement of the fastener in order to properly seat the fixation rod 40 for connection to another fixation assembly. Mono-axial fixation systems require contouring of the fixation rod 40 to account for the static placement of the fastener assembly. A multi-axial fastener assembly, such as is available with the fastener assembly of the present application, requires less accurate placement of the fastener into the vertebral body as well as less contouring of the fixation rod 40 to achieve proper installation of the spinal fixation system.

When the pressure cap 56 is biased against the fastener head 32, the body 14 can be secured in a mono-axial position in relation to the fastener 12. The pressure cap 56 may be transitioned from a disengaged position, wherein the body 14 retains multi-axial movement in relation to the fastener 12, to a biased position, wherein the body 14 is restricted to mono-axial movement in relation to the fastener 12, by a multitude of mechanisms. For example, as shown in FIGS. 1 and 2, the position of the pressure cap 56 may be adjusted in a longitudinal direction by rotating the proximal portion 16 in relation to the distal portion 18 such that the threaded interface between the two portions causes the pressure cap 56 to travel either distally or proximally, depending on the direction of rotation. When the proximal portion 16 is rotated in a direction such that the pressure cap 56 travels in a distal direction, the pressure cap 56 will eventually engage the fastener head 32. Continued rotation will bias the pressure cap 56 against the fastener head 32 and lock the body 14 in a biased, mono-axial position.

Figure 3:
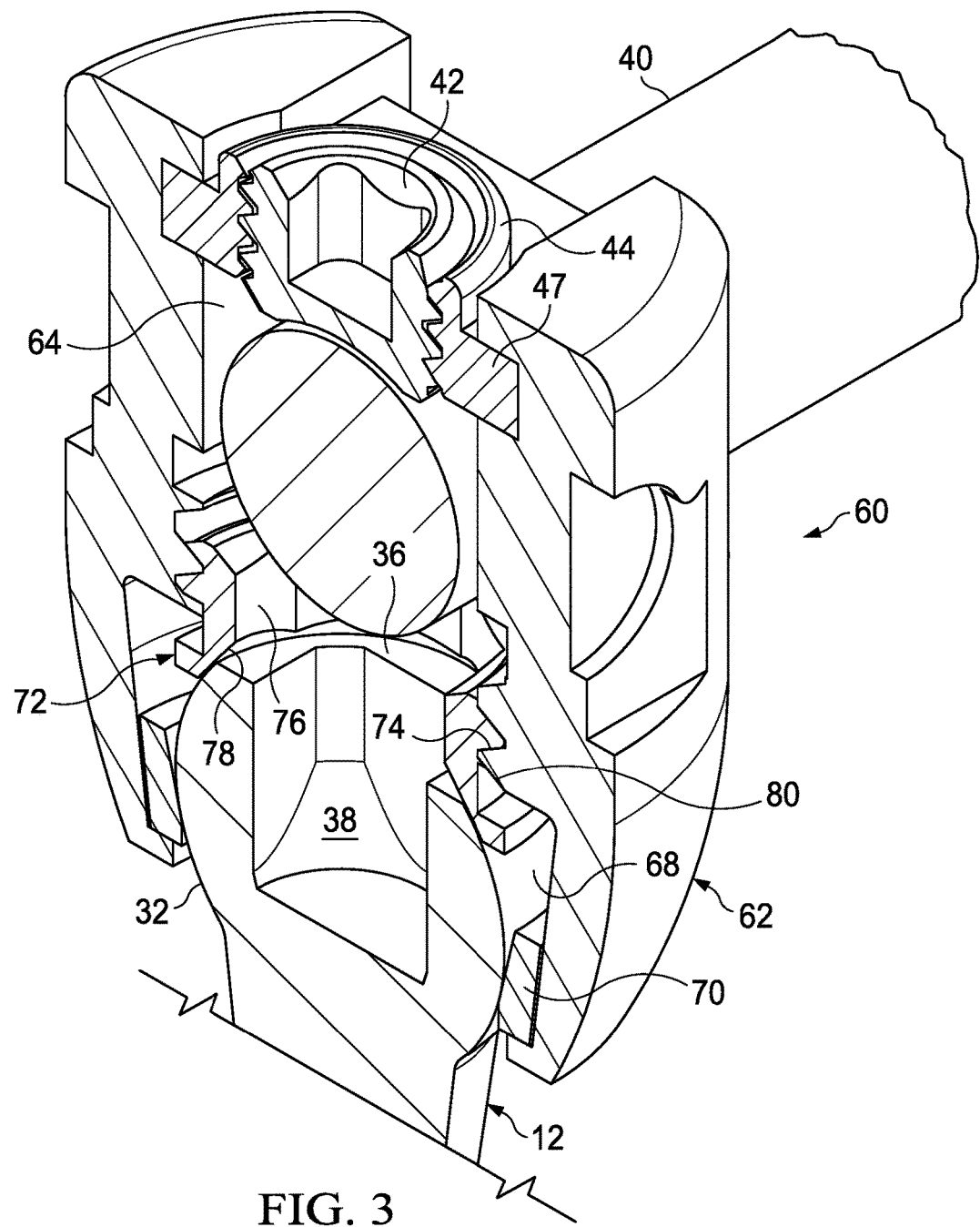
FIG. 3 is a longitudinal cross-sectional view of a lockable fastener assembly and fixation rod.

Referring now to FIG. 3, a longitudinal cross-sectional view of another embodiment of a lockable fastener assembly 60 is shown. In this embodiment the assembly 60 comprises a fastener 12 and a body 62. As in all embodiments, the fastener 12 may be a screw, and more specifically, may be a bone screw. Or the fastener 12 may be any other type of fastener for attachment to a bone. The body 62 includes a rod receiving channel 64 for receiving a fixation rod 40.

As can be seen in the embodiment shown in FIG. 3, the body 62 also includes a fastener head receiving chamber 68 for receiving the head 32 of a fastener 12. The fastener head receiving chamber 68 may have a tapered shape that narrows at the distal end of the fastener head receiving chamber 68 to fit against the fastener head 32. A layer of retaining material 70 may line the interior surface of the fastener head receiving chamber 68, wherein the retaining material is operable to facilitate retention of the fastener head 32 within the fastener head receiving chamber 68. The retaining material 70 may be composed of a softer grade of material than the material composition of the body 62 and may provide a friction fit between the fastener head receiving chamber 68 and the fastener head 32. In certain embodiments, the fastener head receiving chamber 68 may further comprise a constriction element, such as a spring-clip, that operates to create a friction fit between an interior surface of the fastener head receiving chamber 68 and the fastener head 32. In one embodiment, the fastener head 32 may have a substantially spherical shape, wherein the substantially spherical shape may include a flattened proximal face 36, as shown in FIG. 3. In one embodiment, the fastener head 32 may include a drive tool receiving recess 38 for receiving a drive tool which operates to drive the fastener 12 into the bone. The rod receiving channel 64 and the fastener head receiving chamber 68 may be operatively connected to allow a drive tool to pass through to the fastener head 32 and apply torque thereto.

Also shown in FIG. 3 is the fixation rod 40 positioned in the rod receiving channel 64. The fixation rod 40 rests at the distal end of the rod receiving channel 64. The fixation rod 40 can be secured in place in the rod receiving channel 64 using a compression element such as the set screw 42 shown in FIG. 3. The set screw 42 may be attached to a blocker 44 that is inserted into a blocker receiving portion 47 of the proximal portion 16. The set screw 42 may include external threads 46 for engaging internal threads 48 of the blocker. In this embodiment the set screw 42 can be engaged by a drive tool for tightening against the fixation rod 40. In this way, the set screw 42 is operable to retain the fixation rod 40 in the rod receiving channel 64 and secure the fixation rod 40 in a fixed position. In other embodiments, the set screw 42 may be attached to the blocker 44 by attachment means other than internal and external threads. And in further embodiments, the compression element for retaining the rod in a fixed position may be comprised of a mechanism other than a set screw and blocker combination. For example, in some embodiments, the body 62 may include internal threads disposed adjacent to the proximal end of the rod receiving channel 64. A set screw may then attach directly to the body 62 by attachment via its own external threads to the body's internal threads, without the need for a blocker. In even further embodiments, the compression element may be configured as a cap that attaches to the proximal end of the body 62.

The assembly 60 shown in FIG. 3 also includes a pressure cap 72. The pressure cap 72 is comprised of an external attachment feature 74, a proximal interior drive tool receiving surface 76, and a distal interior surface 78 that is contoured to fit against the fastener head 32. For example, when the fastener head 32 has a substantially spherical shape as shown in FIG. 3, the distal interior surface 78 of the pressure cap 72 will be contoured to fit against the substantially spherical surface of the fastener head 32.

As shown in FIG. 3, the body 62 may have an internal attachment feature 80 that engages the external attachment feature 74 of the pressure cap 72. The engagement of the internal attachment feature 80 with the external attachment feature 74 secures the pressure cap 72 to the body 62. In one embodiment, the external attachment feature 74 is an external thread and the internal attachment feature 80 is an internal thread. Such threads could be of any variety of attachment threads, such as buttress threads or any other thread common in the medical industry.

When the pressure cap 72 is disengaged from the fastener head 32, the fit between the distal interior surface 78 of the pressure cap 72 and the fastener head 32 allows the body 62 to pivot along multiple axes in relation to the fastener 12. This multi-axial movement allows the fastener to be placed in the vertebral body much easier than a mono-axial fixation system. A mono-axial fixation system requires very accurate placement of the fastener in order to properly seat the fixation rod 40 for connection to another fixation assembly. Mono-axial fixation systems require contouring of the fixation rod 40 to account for the static placement of the fastener assembly. A multi-axial fastener assembly, such as is available with the fastener assembly of the present application, requires less accurate placement of the fastener into the vertebral body as well as less contouring of the fixation rod 40 to achieve proper installation of the spinal fixation system.

When the pressure cap 72 is biased against the fastener head 32, the body 62 can be secured in a mono-axial position in relation to the fastener 12. The pressure cap 72 may be transitioned from a disengaged position, wherein the body 62 retains multi-axial movement in relation to the fastener 12, to a biased position, wherein the body 62 is restricted to mono-axial movement in relation to the fastener 12, by a multitude of mechanisms. For example, as shown in FIG. 3, the position of the pressure cap 72 may be adjusted in a longitudinal direction by rotating the pressure cap 72 in relation to the body 62 such that the threaded interface between the pressure cap 72 and the body 62 causes the pressure cap 72 to travel either distally or proximally, depending on the direction of rotation. Rotation of the pressure cap may be accomplished by passing a driving tool through the rod receiving chamber 64 and engaging the proximal interior drive tool receiving surface 76 of the pressure cap 72 and rotating said driving tool in a clockwise or counter-clockwise direction. When the pressure cap 72 is rotated in a direction such that the pressure cap 72 travels in a distal direction, the pressure cap 72 will eventually engage the fastener head 32. Continued rotation will bias the pressure cap 72 against the fastener head 32 and lock the body 62 in a biased, mono-axial position.

Figure 4:
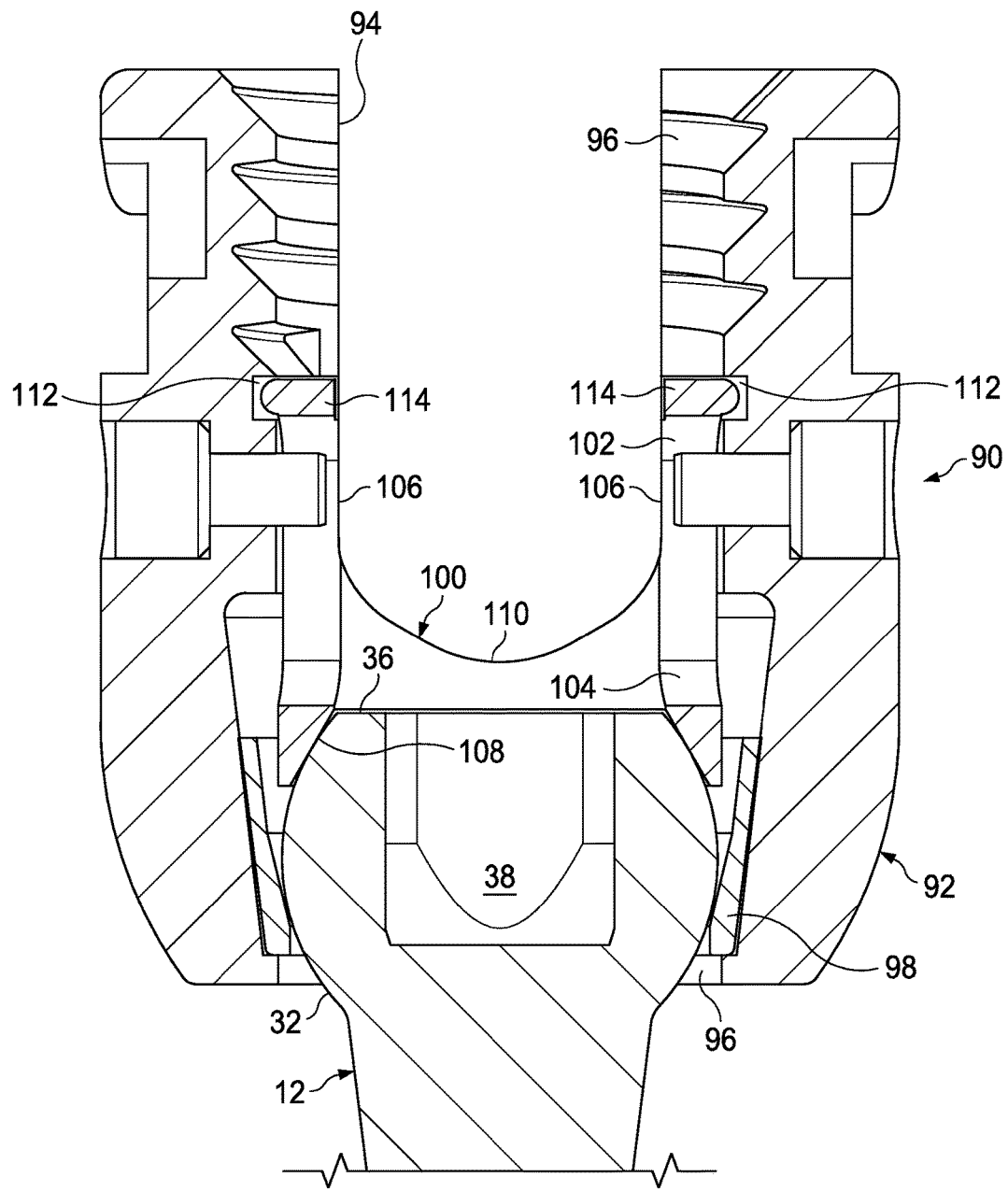
FIG. 4 is a longitudinal cross-sectional view of a lockable fastener assembly.

Referring now to FIG. 4, a longitudinal cross-sectional view of another embodiment of a lockable fastener assembly 90 is shown. In this embodiment the assembly 90 comprises a fastener 12 and a body 92. The body 92 includes a rod receiving channel 94 for receiving a fixation rod. As in all embodiments, the fastener 12 may be a screw, and more specifically, may be a bone screw. Or the fastener 12 may be any other type of fastener for attachment to a bone.

As can be seen in the embodiment shown in FIG. 4, the body 92 also includes a fastener head receiving chamber 96 for receiving the head 32 of a fastener 12. The fastener head receiving chamber 96 may have a tapered shape that narrows at the distal end of the fastener head receiving chamber 96 to fit against the fastener head 32. A layer of retaining material 98 may line the interior surface of the fastener head receiving chamber 96, wherein the retaining material is operable to facilitate retention of the fastener head 32 within the fastener head receiving chamber 96. The retaining material 98 may be composed of a softer grade of material than the material composition of the body 92 and may provide a friction fit between the fastener head receiving chamber 96 and the fastener head 32. In one embodiment, the fastener head 32 may have a substantially spherical shape, wherein the substantially spherical shape may include a flattened proximal face 36, as shown in FIG. 4. In one embodiment, the fastener head 32 may include a drive tool receiving recess 38 for receiving a drive tool which operates to drive the fastener into the bone. The rod receiving channel 94 and the fastener head receiving chamber 96 may be operatively connected to allow a drive tool to pass through to the fastener head 32 and apply torque thereto.

Although not shown in FIG. 4, a fixation rod may be placed to rest at the distal end of the rod receiving channel 94, similar to what is shown in the embodiments of FIGS. 2 and 3. The fixation rod can be secured in place in the rod receiving channel 94 using a compression element such as the set screw 42 shown in FIG. 2. The set screw may be attached to a blocker that is inserted into a blocker receiving portion of the proximal portion of the body 92. Alternatively, as is shown in FIG. 4, the proximal portion of the body 92 may include internal threads for engaging the external threads of a set screw, thereby eliminating the need for the blocker. In either embodiment the set screw can be engaged by a drive tool for tightening against the fixation rod. In this way, the set screw is operable to retain the fixation rod in the rod receiving channel 94 and secure the fixation rod in a fixed position. In other embodiments, the set screw may be attached to the body 92, or a blocker, by attachment means other than internal and external threads. And in further embodiments, the compression element for retaining the rod in a fixed position may be comprised of a mechanism other than a set screw and blocker combination. For example, the compression element may be configured as a cap that attaches to the proximal end of the body 92.

The assembly 90 shown in FIG. 4 also includes a pressure cap 100. The pressure cap 100 is comprised of a proximal portion 102 disposed at least partially within the screw rod receiving channel 94, a distal portion 104 disposed at least partially within the fastener head receiving chamber 96, and at least two lateral sides 106 extending from the proximal portion to the distal portion. The distal portion 104 of the pressure cap 100 comprises a distal interior surface 108 for interfacing the fastener head 32. The distal interior surface 108 may be contoured to fit against the fastener head 32. For example, when the fastener head 32 has a substantially spherical shape as shown in FIG. 4, the distal interior surface 108 of the pressure cap 100 will be contoured to fit against the substantially spherical surface of the fastener head 32. The pressure cap 100 also comprises a rod receiving surface 110 located at least partially proximal to the distal interior surface 108. An aperture extending approximately between the rod receiving surface 110 and the distal interior surface 108 allows a drive tool to pass through the pressure cap for engaging the drive tool receiving recess 38 of the fastener head 32. Once engaged, the drive tool can be used to attach the fastener 12 to the bone.

When the pressure cap 100 is disengaged from the fastener head 32, the fit between the distal interior surface 108 of the pressure cap 100 and the fastener head 32 allows the body 92 to pivot along multiple axes in relation to the fastener 12. This multi-axial movement allows the fastener to be placed in the vertebral body much easier than a mono-axial fixation system. A mono-axial fixation system requires very accurate placement of the fastener in order to properly seat the fixation rod for connection to another fixation assembly. Mono-axial fixation systems require contouring of the fixation rod to account for the static placement of the fastener assembly. A multi-axial fastener assembly, such as is available with the fastener assembly of the present application, requires less accurate placement of the fastener into the vertebral body as well as less contouring of the fixation rod to achieve proper installation of the spinal fixation system.

The pressure cap 100 can travel in a longitudinal direction, either proximally or distally. When the pressure cap 100 is in a disengaged position, the pressure cap 100 can be moved in a distal direction by applying a pressure to the rod receiving surface 110 using a tool or a fixation rod in contact with the rod receiving surface 110. As the pressure 100 cap travels distally, the distal interior surface 108 of the pressure cap 110 will become biased against the fastener head 32.

When the pressure cap 100 is biased against the fastener head 32, the body 92 can be secured in a mono-axial position in relation to the fastener 12. The pressure cap 100 may be transitioned from a disengaged position, wherein the body 92 retains multi-axial movement in relation to the fastener 12, to a biased position, wherein the body 92 is restricted to mono-axial movement in relation to the fastener 12. For example, the pressure cap 100 shown in FIG. 4 can travel in a longitudinal direction, either proximally or distally. When the pressure cap 100 starts in a disengaged position, the pressure cap 100 can be moved in a distal direction by applying a pressure to the rod receiving surface 110 using a tool or a fixation rod in contact with the rod receiving surface 110. As the pressure cap 100 travels distally, the distal interior surface 108 of the pressure cap 110 will engage the fastener head 32. Continued pressure on the rod receiving surface 110 will bias the pressure cap 100 against the fastener head 32 and place the body 92 in a biased, mono-axial position.

In some embodiments, the fastener assembly 90 also comprises a locking mechanism for securing the pressure cap 100 in a biased position, thereby locking the body 92 in a mono-axial state. One example can be seen in FIG. 4, wherein the lateral walls of the rod receiving chamber 94 each include an undercut 112. The lateral sides 106 of the pressure cap each include a flange 114 located at the proximal end of the sides 106. When the pressure cap 100 travels distally to a point where the distal interior surface 108 is biased against the fastener head 32, the flanges 106 will engage the undercuts 112 and lock the pressure cap 100 in a biased position.

Figure 5:
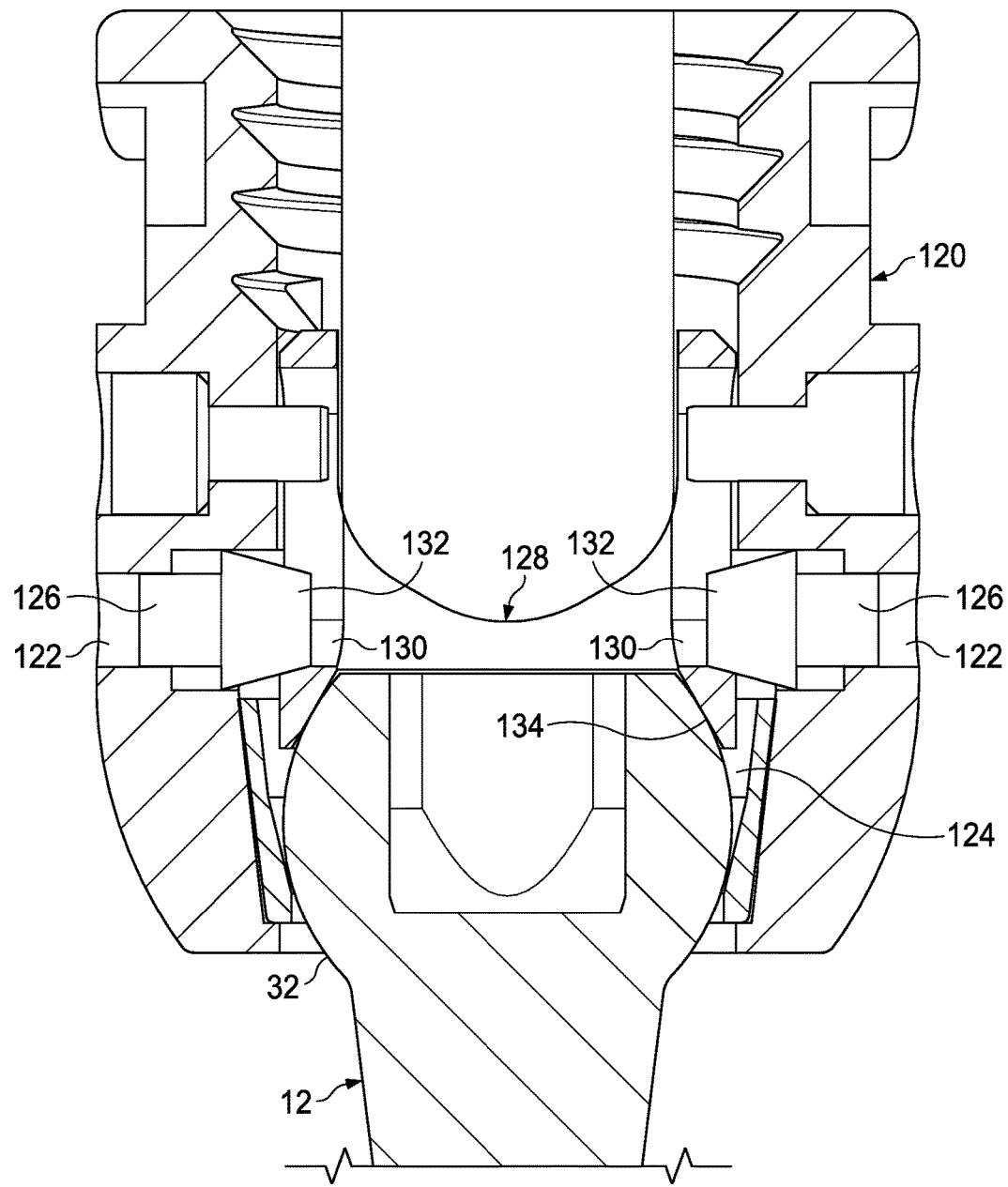
FIG. 5 is a longitudinal cross-sectional view of a lockable fastener assembly.

Another embodiment of a locking mechanism is shown in FIG. 5. As part of the locking mechanism, the lateral walls of the body 120 include bores 122. The bores 122 extend from the exterior lateral wall of the body 120 to the interior lateral wall of the fastener head receiving chamber 124. The bores 122 are generally located at the proximal end of the fastener head receiving chamber 124. The locking mechanism further comprises a wedge element 126 located within each bore 122, that is operable to travel laterally within the bore 122. The wedge element 126 may be in the form of a tapered locking pin, as shown in FIG. 5. Other embodiments of the wedge element 126 may include a cam or a sphere that fits within the bores. The pressure cap 128 has a recess 130 for interfacing to each bore 122 within the body 120. The recesses 130 can be either a partial recess or a full bore that extends from the outer surface to the inner surface of the pressure cap 128. When pressure is applied to the wedge element 126 in a medial direction, the medial end 132 of the wedge element is forced between the proximal surface of the bore 122 within which the wedge element 126 resides and the distal surface of the recess 130 associated with the bore 122. Any instrument providing penetrating access to the bores from the exterior may be used for applying the medial pressure. By applying the medial pressure, the wedge element 126 is lodged between the two surfaces into a wedged position. In the wedged position, the wedge element 126 applies a bias in the distal direction to the pressure cap 128, which thereby locks the pressure cap 128 in a biased position. In the biased position, the distal interior surface 134 is biased against the fastener head 32 and secures the body 120 in a mono-axial state.

Figure 6:
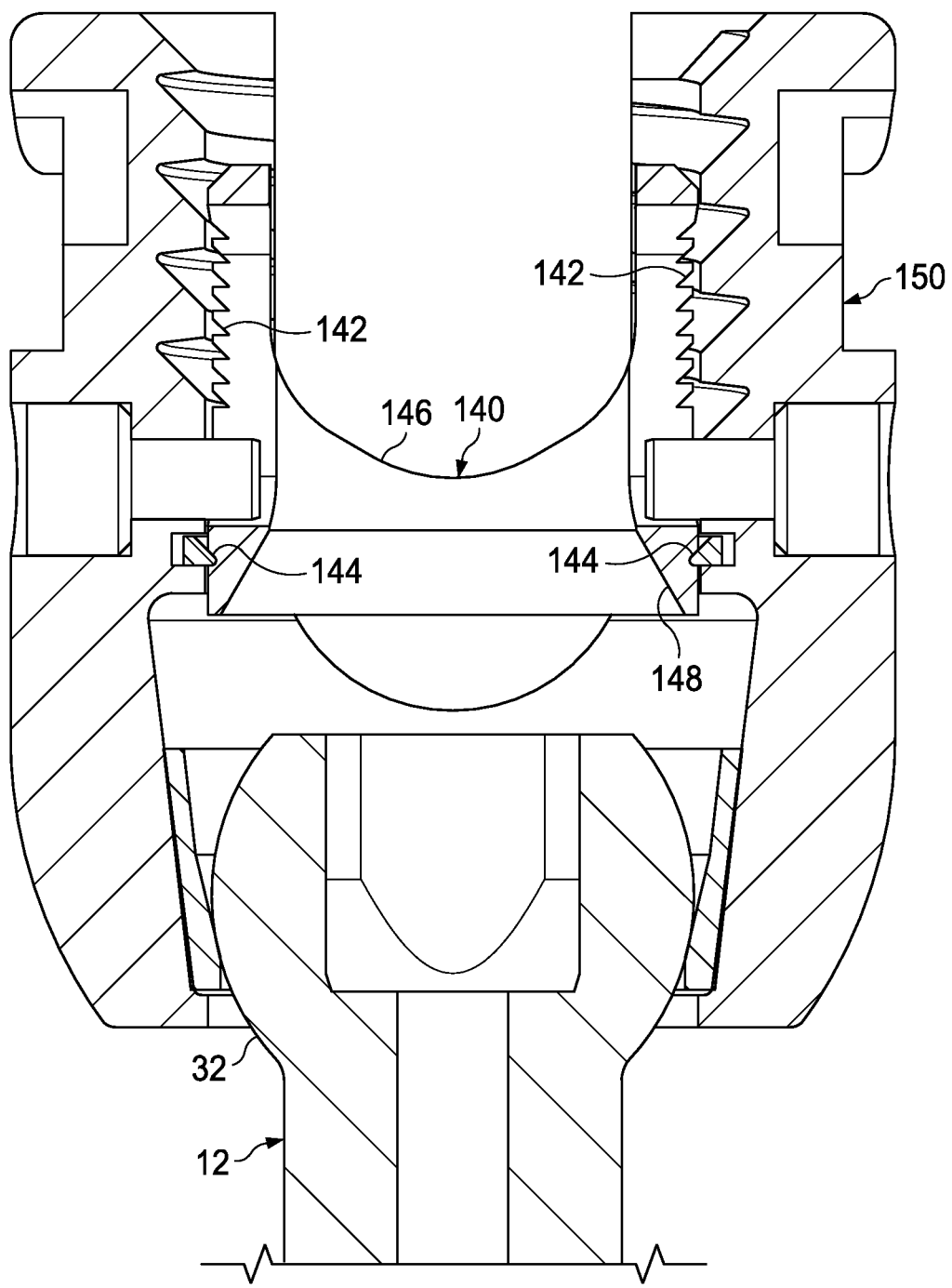
FIG. 6 is a longitudinal cross-sectional view of a lockable fastener assembly.
Figure 7:
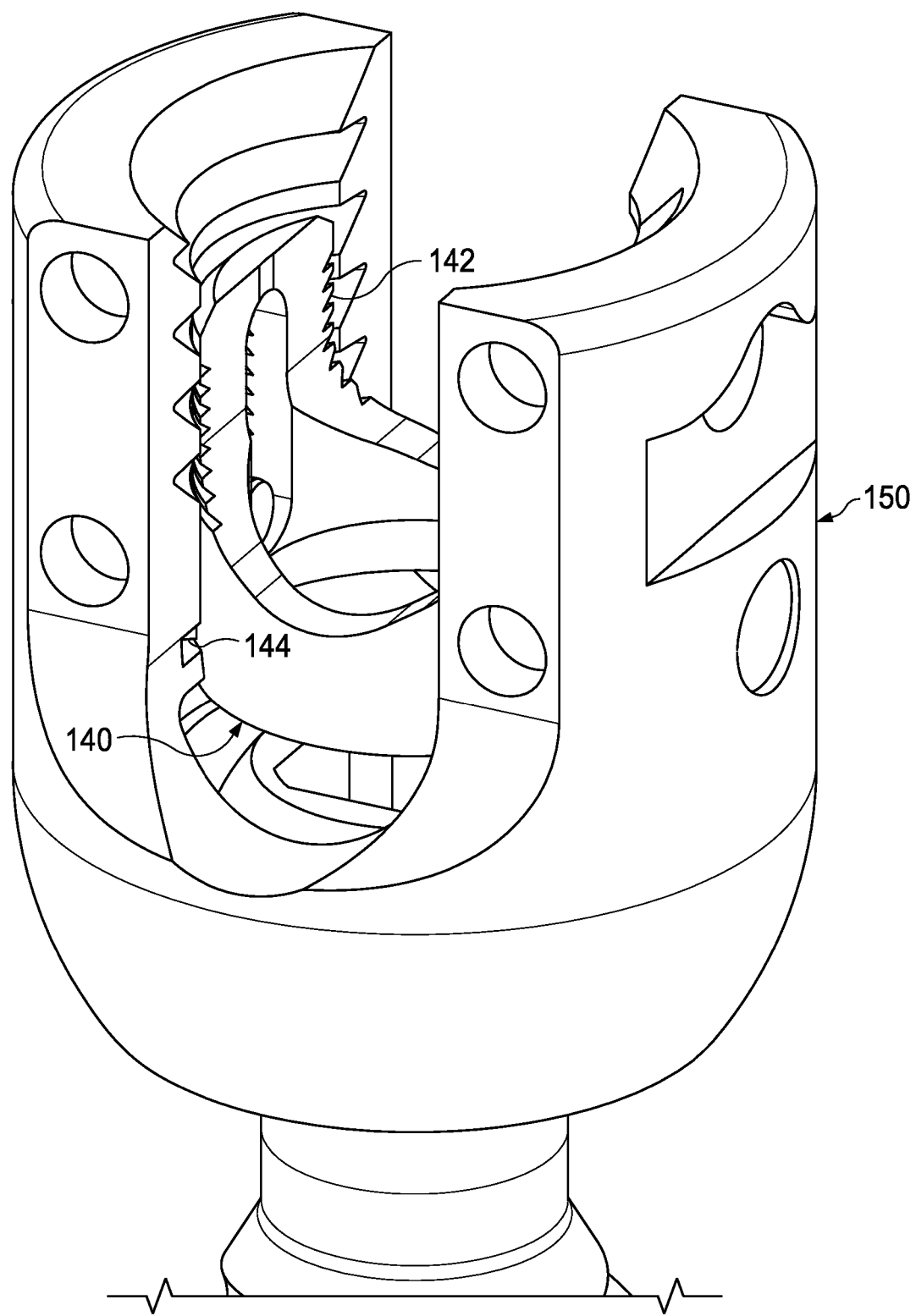
FIG. 7 is a perspective view of a lockable fastener assembly.

Yet another embodiment of a locking mechanism is shown in FIG. 6. The exterior surface of the lateral sides of the pressure cap 140 have a linear rack of one or more teeth 142. The lateral walls of the rod receiving channel also include one or more pawls 144 operable to engage the one or more teeth 142 of the pressure cap 140. FIG. 7 illustrates a perspective view of the assembly with the pressure cap 140 in a disengaged position. The pressure cap 140 may travel distally by applying pressure to the rod receiving surface 146 with a tool or fixation rod such that the distal interior surface 148 of the pressure cap 140 is biased against the fastener head 32. When the distal interior surface 148 is biased against the fastener head 32, the body 150 will be secured in a mono-axial state in relation to the fastener 12. The pawls 144 will engage the teeth 142 of the pressure cap 140, thereby locking the pressure cap 140 in a biased position against the fastener head 32. In some embodiments, the teeth 142 of the pressure cap 140 will be asymmetrical in shape such that each tooth has a moderate slope on a distal edge and a much steeper slope on a proximal edge. Thus, the interaction between the teeth 142 and the pawls 144 will act as a ratcheting system such that the interaction allows the pressure cap 140 to travel distally, but prohibits the pressure cap 140 from traveling in the proximal direction. The pawls 144 may be spring-loaded to accomplish this interaction. A release system could then be used to retract the pawls 144 and thereby allow the pressure cap 140 to travel proximally.

All embodiments of the fastener assembly can be delivered to the user and surgically implanted in either pre-assembled form or modular form. The elements of the fastener assembly can be manufactured from any medical-grade material suitable for its purpose.

Although the embodiments described and claimed herein have been described in considerable detail with reference to certain embodiments, one skilled in the art will appreciate that the inventions described and claimed herein can be practiced by other than those embodiments, which have been presented for purposes of illustration and not of limitation. Therefore, the spirit and scope of the appended claims should not be limited to the description of the embodiments contained herein.

What is claimed is:

1. A spinal fixation system, comprising:
   at least one screw having a screw head at a proximal end and wherein the screw head comprises a substantially spherical surface;
   at least one body, wherein the body has a proximal portion and a distal portion;
   the proximal portion comprising:
      a rod receiving channel operable to receive a fixation rod;
      an external attachment feature; and
      a pressure cap disposed at a distal end of the proximal portion and formed integrally with the proximal portion, wherein a distal end of the pressure cap comprises an interior surface contoured to fit against the substantially spherical surface of the screw head;
   the distal portion comprising:
      an internal attachment feature operable to engage the external attachment feature of the proximal portion, wherein the engaging of the internal attachment feature with the external attachment feature secures the proximal portion to the distal portion;
      a screw head receiving chamber disposed at a distal end of the distal portion operable to retain the screw head within the body; and
      an external surface operable to engage a drive tool that operates to join the internal attachment feature with the external attachment feature and further cause the pressure cap to apply a bias against the screw head;
   wherein a majority of a diameter of the external surface is greater than an outer diameter of the proximal portion;
   wherein the screw head receiving chamber allows multi-axial movement of the body in relation to the screw when the pressure cap is disengaged from the screw head; and wherein the difference in diameter between the external surface and the proximal portion allows the body to be secured in a mono-axial position in relation to the screw when the external surface is engaged after the pressure cap has been biased against the screw head.

2. The spinal fixation system of claim 1, further comprising:
a compression element disposed at a proximal end of the rod receiving channel wherein the compression element is operable to apply a bias to a proximal surface of the fixation rod and thereby retain the fixation rod within the rod receiving channel.

3. The spinal fixation system of claim 2, wherein the compression element comprises a set screw having external threads operable to cooperate with complementary internal threads, wherein the complementary internal threads are disposed on the proximal portion of the body or on a blocker inserted into a blocker receiving portion on the proximal portion of the body.

4. The spinal fixation system of claim 1, wherein the external attachment feature of the proximal portion of the body comprises external threads and the internal attachment feature of the distal portion of the body comprises complementary internal threads.

5. The spinal fixation system of claim 1, wherein the external surface of the distal portion of the body comprises a perimeter of three or more flat sides operable to engage the drive tool.

6. The spinal fixation system of claim 1, wherein the at least one screw is a bone screw.

7. The spinal fixation system of claim 6, wherein the at least one bone screw is configured to be screwed into a pedicle portion of a spine.

8. The spinal fixation system of claim 1, wherein the rod receiving channel and the screw head receiving chamber are operatively connected to allow a tool to be inserted therethrough to apply torque to the screw.

9. The spinal fixation system of claim 1, wherein the screw head receiving chamber includes a constriction element that operates to create a friction fit between an interior surface of the screw head receiving chamber and the substantially spherical surface of the screw head.

10. A spinal fixation system, comprising:
at least one screw having a screw head at a proximal end and wherein the screw head comprises a substantially spherical surface;
at least one body, the body having a proximal end and a distal end and further comprising:
a rod receiving channel operable to receive a fixation rod wherein the rod receiving channel is disposed adjacent the proximal end of the body;
an engagement feature disposed at the proximal end of the body;
a screw head receiving chamber disposed adjacent the distal end of the body; and
an internal thread disposed at the distal end of the body;
wherein the rod receiving channel and the screw head receiving chamber are operatively connected;
a fastener operable to engage the engagement feature to secure the rod in the rod receiving channel;
a pressure cap operable to engage the screw head, the pressure cap comprising:
a proximal portion disposed at least partially within the rod receiving channel;
a distal portion disposed at least partially within the screw head receiving chamber;
at least two lateral sides extending from the proximal portion to the distal portion;
a screw head interface disposed adjacent to the distal portion of the pressure cap;
a rod receiving surface disposed proximal to the screw head interface;
an aperture extending from the rod receiving surface to the screw head interface; and
an external thread operable to cooperate with the internal thread of the body to provide a threaded interface;
wherein when a tool is used to rotate the pressure cap the threaded interface causes the pressure cap to travel distally, independent of the fastener, such that the screw head interface of the pressure cap is biased against the screw head in the screw head receiving chamber to secure the body in a mono-axial position in relation to the screw; and
wherein the screw head receiving chamber allows multiaxial movement of the body in relation to the screw when the pressure cap is disengaged from the screw head.

11. The spinal fixation system of claim 10, wherein
the engagement feature comprises internal threads, and
the fastener comprises a set screw having external threads operable to cooperate with the internal threads of the engagement feature.

12. The spinal fixation system of claim 10, wherein the at least one screw is a bone screw.

13. The spinal fixation system of claim 12, wherein the at least one bone screw is configured to be screwed into a pedicle portion of a spine.

14. The spinal fixation system of claim 10, wherein the aperture extending from the rod receiving surface to the screw head interface is operable to allow a tool to be inserted therethrough to apply torque to the screw.

15. The spinal fixation system of claim 10, wherein the screw head receiving chamber includes a constriction element that operates to create a friction fit between an interior surface of the screw head receiving chamber and the substantially spherical surface of the screw head.

* * * * *